United States Patent
Lazarevski et al.

Patent Number: 6,077,944
Date of Patent: Jun. 20, 2000

[54] SECOMACROLIDES FROM CLASS OF ERYTHROMYCINS AND PROCESS FOR THEIR PREPARATION

[75] Inventors: Gorjana Lazarevski; Gabrijela Kobrehel; Amalija Narandja; Zrinka Banić-Tomišič, all of Zagreb, Croatia

[73] Assignee: Pliva Farmaceutska, Kemijska, Prehrambena i Kozmeticka Industrija, Dionicko Drustvo, Zagreb, Croatia

[21] Appl. No.: 09/038,901

[22] Filed: Mar. 12, 1998

[30] Foreign Application Priority Data

Mar. 12, 1997 [HR] Croatia ................. P970141A

[51] Int. Cl.⁷ ................. C07H 1/00; C07H 15/00
[52] U.S. Cl. ............. 536/17.9; 536/4.1; 536/7.4; 536/17.2; 536/18.5; 564/123
[58] Field of Search .............. 536/4.1, 7.4, 17.2, 536/17.9, 18.5; 564/123

[56] References Cited

U.S. PATENT DOCUMENTS 5,721,346 2/1998 Lazarevsky et al. ............ 536/17.9

*Primary Examiner*—Elli Peselev
*Attorney, Agent, or Firm*—Pollock, Vande Sande & Amernick

[57] ABSTRACT

The invention relates to novel secomacrolides from the class of erythromycin A, potential intermediates for preparation of novel macrolide antibiotics general formula

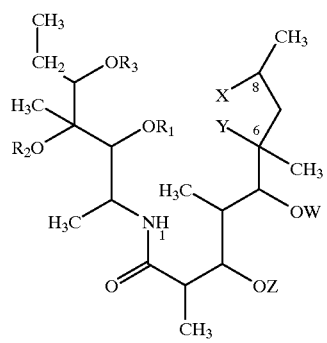

(I)

and its pharmaceuticaly acceptable addition salts with inorganic or organic acids, wherein $R_1$ represents hydrogen, $C_1$–$C_4$ alkanoyl group, arylcarbonyl group and together with $R_2$ and carbon atoms to which they are bound, cyclic carbonyl or thiocarbonyl group, $R_2$ represents hydrogen or together with $R_1$ and carbon atoms to which they are bound, cyclic carbonyl or thiocarbonyl group, $R_3$ represents hydrogen, $C_1$–$C_4$ alkanoyl or arylcarbonyl group, Z is hydrogen or L-cladinosyl group represented by formula (i)

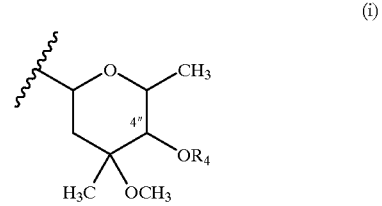

wherein $R_4$ represents hydrogen or $C_1$–$C_4$ alkanoyl group,

W is hydrogen or D-desosaminyl group represented by formula (ii)

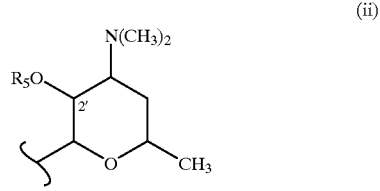

wherein $R_5$ represents hydrogen or $C_1$–$C_4$ alkanoyl or arylcarbonyl group, X and Y together represent a lactone, or X is $CH_2OR_6$, wherein $R_6$ represents hydrogen or $C_1$–$C_4$ alkanoyl group and Y is hydroxyl group.

35 Claims, No Drawings

SECOMACROLIDES FROM CLASS OF ERYTHROMYCINS AND PROCESS FOR THEIR PREPARATION

TECHNICAL FIELD OF THE INVENTION

A6 I K 3 1/70, C07H 17/08

TECHNICAL PROBLEM

The invention relates to novel compounds from the class of the well-known macrolide antibiotic erythromycin A. Particularly, the invention relates to novel secomacrolides, potential intermediates for the preparation of novel macrolides with antibacterial action as well as to a process for their preparation.

PRIOR ART

Erythromycin A is a macrolide antibiotic, whose structure is characterized by a 14-membered lactone ring with C-9 ketone and two sugars, L-cladinose and D-desosamine, glycosydically bound in C-3 and C-5 positions onto an aglycone moiety of the molecule (McGuire, Antibiot. Chemother. 1952; 2:281). For more than 40 years it has been considered as a safe and effective antimicrobial agent in the treatment of respiratory and genital infections caused by gram-positive bacteria, some species of Legionella, Mycoplasma, Chlamidia and Helicobacter. Noticeable changes in bioavailability after application of oral preparations, gastric intolerance in many patients and loss of activity in acidic medium under formation of inactive metabolite anhydroerythromycin are the basic disadvantages in the therapeutic use of erythromycin A. However, spirocyclization of the aglycone ring is successfully inhibited by a chemical transformation of C-9 ketone or hydroxyl groups in C-6 and/or C-12 position. Thus, for example, by an oximation of C-9 ketone of erythromycin A with hydroxylamine hydrochloride, by Beckmann rearrangement of the obtained 9(E)-oxime and a reduction of the formed 6,9-imino ether (6-deoxy-9-deoxo-9a-aza-homoerythromycin A 6,9-cyclic imino ether) there is obtained 9-deoxo- 9a-aza-9a-homoerythromycin A, the first semi synthetic macrolide with a 15-membered azalactone ring (Kobrehel G. et al., U.S. Pat. No. 4,328,334, May 1982). According to Eschweiler-Clark process, by means of a reductive methylation of the newly introduced endocyclic 9a-amino group, 9-deoxo-9a-methyl-9a-aza-9a-homo-erythromycin A (AZITHROMYCIN), a prototype of a novel class of azalide antibiotics was synthesized (Kobrehel G. et al., BE 892 357, July 1982). In addition to having a broad antimicrobial spectrum including also gram-negative bacteria, azithromycin is also characterized by a long biological half-life, a specific transport mechanism to the site of use and a short therapy time. Azithromycin easily penetrates nad accumulates inside human fagocyte cells resulting in improved activity on intracellular pathogenic microorganisms from classes Legionella, Chlamydia and Helicobacter.

Recently, hydrolysis and alcoholysis of C-1 lactone of erythromycin A and B, whereby corresponding linear secoacids and esters were formed, were described (Martin S., J. Am. Chem. Soc., 1991; 113: 5478). Further, there was also described an alkaline-catalyzed transformation of erythromycin A leading to the opening of a macrocyclic ring under formation of C-1 carboxylate (Waddel S. T. and Blizzard T. A., PCT, WO 94/15617, July 1994). Described was also a method for the preparation of novel macrolide and azalide rings by a combination of the eastern C-1/C-8 and C-1/C-9 moieties of the molecules of 9-deoxo-8a-aza-8a-homoerythromycin A and 9-deoxo-9a-aza-9a-homoerythromycin A, respectively, with different fragments that become the western moiety of the molecule. It has to be pointed out that C-1/C-9 linear fragments obtained in such a manner differ from the corresponding fragment in azithromycin by an additional ethyl group on C-9 carbon atom. In EP 0 735 041 A1 (Lazarevski G. et al., February 1996) there was described a synthesis of novel secoazalides by the action of hydroxylamine hydrochloride upon 6,9-cyclic imino ether and by subsequent alkaline-catalyzed internal acylation of a newly formed C-10 amino group and C-1 lactone. The structure of so obtained C-1 amides is characterized by an eastern C-1/C-9 fragment which is identical to the one in azithromycin and a western C-10/C-15 fragment of erythromycin A inversely bound to C-1 carbon atom. However, by the action of acids upon 6,9-cyclic imino ether under cleaving of C-9/9 a-N double bond, 6-deoxy-6,9-epoxy-8(R)-methyl-10-amino-9,10-secoerythromycin A with the terminal C-10 group is formed. The subject of the present invention is the syntesis of novel secomacrolides, potential intermediates in the synthesis of biologically active chimeric macrolides starting from 6-deoxy-6,9-epoxy-8(R)-methyl-10-amino-9,10-seco-erythromycin A.

SUMMARY OF THE INVENTION

According to the known and established prior art secomacrolides of general formula (I),

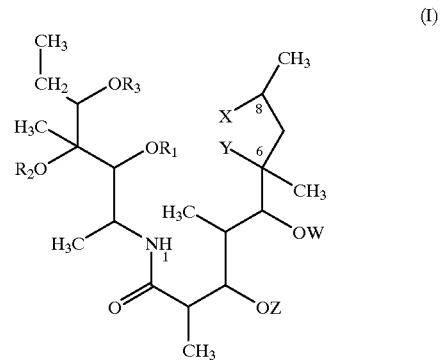

wherein $R_1$ represents hydrogen, $C_1$–$C_4$ alkanoyl group, arylcarbonyl group or, together with $R_2$ and carbon atoms to which they are bound, cyclic carbonyl or thiocarbonyl group, $R_2$ represents hydrogen or, together with $R_1$ and carbon atoms to which they are bound, cyclic carbonyl or thiocarbonyl group, $R_3$ represents hydrogen, $C_1$–$C_4$ alkanoyl or arylcarbonyl group, Z is hydrogen or L-cladinosyl group represented by formula (i)

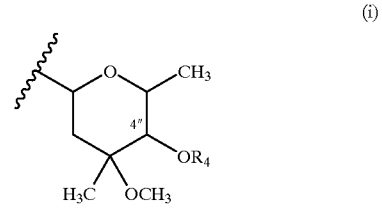

wherein $R_4$ represents hydrogen or $C_1$–$C_4$ alkanoyl group, W is hydrogen or D-desosaminyl group represented by formula (ii)

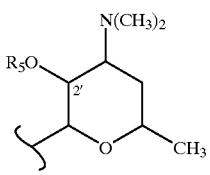

wherein $R_5$ represents hydrogen or $C_1$–$C_4$ alkanoyl or arylcarbonyl group, X and Y together represent lactone or X is $CH_2OR_6$ group, wherein $R_6$ represents hydrogen or $C_1$–$C_4$ alkanoyl group and Y is hydroxyl group, have hitherto not been described. The invention also relates to their pharmaceutically acceptable addition salts with inorganic or organic acids.

DETAILED DESCRIPTION OF THE INVENTION

Novel secomacrolides of general formula (I),

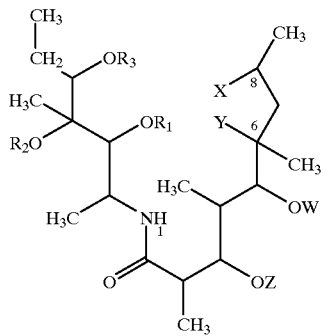

wherein X, Y, Z and W have the meanings as given above and their pharmaceutically acceptable addition salts with inorganic or organic acids are obtained by subjecting 6-deoxy-6,9-epoxy-8(R)-methyl-10-amino-9,10-secoerythromycin A (EP 0 735 041 A1, February 1996) of formula (II)

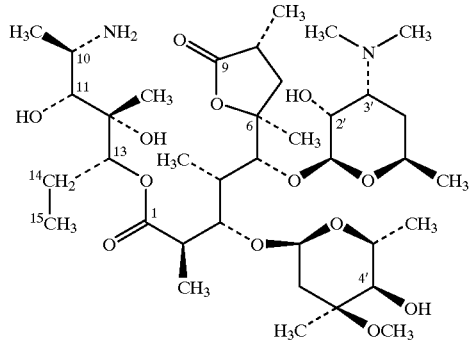

to the reaction with polar solvents for a period of time required that by inert acylation of the primary C-10 amino group and C-1 lactone a compound of the general formula (I) is formed, wherein R $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ is hydrogen, and X and Y together represent lactone [compound (Ia)], which is subsequently subjected to A/ a reaction with acids under the condition of hydrolysis of one or both sugars, yielding a compound of the general formula (I), wherein $R_1$, $R_2$ and $R_3$ are the same and represent hydrogen, Z is hydrogen, W is D-desosaminyl group represented by formula (ii), wherein $R_5$ is hydrogen, and X and Y together represent lactone [compound (Ib)] and a compound of the general formula (I), wherein $R_1$, $R_2$ and $R_3$ are the same and represent hydrogen, Z and W are the same and represent hydrogen, and X and Y together represent lactone [compound (Ic)], or B/ O-acylation with anhydrides or chlorides of carboxylic acids, yielding B1/ by O-acylation with anhydrides or chlorides of $C_1$–$C_4$ alkylcarboxylic acids, a compound of the general formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ represents $C_1$–$C_4$ alkanoyl group, and X and Y together represent lactone, which is subsequently, if required, subjected to the reaction of solvolysis, yielding a compound of the general formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ is hydrogen, and X and Y together represent lactone, or yielding B2/ by O-acylation with chlorides of arylcarboxylic acids, in accordance with B2a/ by using at least 1.1 equimolar excess of acid chloride, a compound of the general formula (I), wherein $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ represents arylcarbonyl group, and X and Z together represent lactone, which is, if required, subjected to O-acylation according to B1/, yielding a compound of the general formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ represents arylcarbonyl group, and X and Y together represent lactone, or B2b/ by using at least 5 equimolar excess of acid chloride, a mixture of compounds of the general formula (I), wherein $R_1$ represents arylcarbonyl group, and $R_2$ and $R_3$ are the same and represent hydrogen, or wherein $R_3$ represents arylcarbonyl group and $R_1$ and $R_2$ are the same and represent hydrogen, Z is L-cladinosyl group represented by formula (i), wherein $R_4$ is hydrogen, and W is D-desosaminyl group represented by formula (ii), wherein $R_5$ represents arylcarbonyl group, and X and Y together represent lactone, which compounds are separated by chromatography on a silica gel column and subsequently, if required, subjected to the reaction of solvolysis, yielding a compound of the general formula (I), wherein $R_1$ represents arylcarbonyl group and $R_2$ and $R_3$ are the same and represent hydrogen, or wherein $R_3$ represents arylcarbonyl group and $R_1$ and $R_2$ are the same and represent hydrogen, Z is L-cladinosyl group represented by formula (i), wherein $R_4$ is hydrogen, W is D-desosaminyl group represented by formula (ii), wherein $R_5$ is hydrogen, and X and Y together represent lactone, or C/ a reaction of transesterification with carboxylic acid derivatives, yielding a compound of the general formula (I), wherein $R_1$ and $R_2$ together with carbon atoms, to which they are bound, represent cyclic carbonyl or thiocarbonyl group and $R_3$ is hydrogen, Z is L-cladinosyl group represented by formula (i), wherein $R_4$ is hydrogen, W is D-desosaminyl group represented by formula (ii), wherein $R_5$ is hydrogen, and X and Y together represent lactone, or D/ a reduction, yielding a compound of the general formula (I), wherein $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ is hydrogen, and X is $CH_2OR_6$ group, wherein $R_6$ is hydrogen and Y is hydroxyl group, which is optionally subjected to O-acylation according to B1/ yielding a compound of the general formula (I), wherein $R_1$ and $R_3$ are the same and represent $C_1$–$C_4$ alkanoyl group, $R_2$ is hydrogen, Z is L-cladinosyl group represented by formula (i), wherein $R_4$ is $C_1$–$C_4$ alkanoyl group, W is D-desosaminyl group represented by formula (ii), wherein $R_5$ represents $C_1$–$C_4$ alkanoyl group, X is $CH_2OR_6$ group, wherein $R_6$ represents $C_1$–$C_4$ alkanoyl group and Y is hydroxyl group.

Internal acylation of C-10 amino group with C-1 lactone of the compound (II) is carried out in water or in a mixture of water and an organic solvent, preferably lower alcohols or acetone, at room temperature or increased temperature in order to accelerate the transacylation, according to the known process (March J., Advanced Organic Chemistry: Reactions, Mechanisms and Structure; Third Ed. 1985, p. 375).

The hydrolysis of the compound (Ia) according to A/ is carried out by a well-known process in two steps. In the first step by a reaction with diluted inorganic acids, preferably 0.25 N hydrochloric acid, at room temperature it comes to the cleaving of a neutral sugar, L-cladinose, whereby 5-O-desosaminyl derivative of (Ib) is formed, which is subsequently, if required, subjected to the action of more concentrated acids, preferably 2 to 6 N hydrochloric acid, in the presence of an inert organic solvent, preferably chloroform, at an increased temperature, preferably at reflux temperature of the reaction mixture, whereby under cleavage of the second sugar, D-desosamine, the compound (Ic) is obtained.

The reaction of O-acylation of the compound (Ia) according to B1/ is carried out with anhydrides or chlorides of $C_1$–$C_4$ alkyl-carboxylic acids by a well-known process, in a reaction-inert solvent, at a temperature from 0 to 30° C. in the presence of suitable bases (Jones et al., J. Med. Chem. 1971, 15, 631, and Banaszek et al., Rocy. Chem., 1969, 43, 763). As inert solvents methylene chloride, dichloro ethane, acetone, pyridine, ethyl acetate, tetrahydrofuran and other similar solvents can be used. As suitable bases sodium hydrogen carbonate, sodium carbonate, potassium carbonate, triethylamine, pyridine, tributylamine and some other inorganic and organic bases are used. Thus, e.g. by acylation of (Ia) with acetic acid anhydride in pyridine, at room temperature, for 3 days, tetraacetate (Id) ($R_1$=$R_3$=$R_4$=$R_5$=acetyl, $R_2$ is hydrogen, X and Y together represent lactone) is obtained. A solvolisys of the obtained tetraacyl derivatives is carried out in lower alcohols at room temperature or at an increased temperature in order to accelerate the reaction, whereby a deacylation of 2'-position is carried out. In this case as the lower alcohol methanol, ethanol, propanol or butanol can be used. For example, by leaving tetracetate (Id) to stand in methanol at room temperature for 3 days, triacetate (Ie) ($R_1$=$R_3$=$R_4$=acetyl, $R_2$=$R_5$=hydrogen, X and Y together represent lactone) is formed. O-acylation of the compound (Ia) with chlorides of arylcarboxylic acids according to B2/, wherein by a term aryl unsubstituted or substituted phenyl group, preferably $C_1$–$C_4$ alkylphenyl or halophenyl group, are meant, is preferably carried out in inert solvents, preferably acetone, in the presence of inorganic or organic bases, preferably sodium hydrogen carbonate, whereby, depending on the equimolar ratio of the reactants, the temperature of the reaction and acylation time, corresponding mono- or diarylcarbonyl derivatives are formed. Thus, e.g. by acylation of (Ia) with at least 1.1 equimolar excess of 4-bromobenzoyl chloride in dry acetone, at 0 to 5° C., 2'-monobromobenzoate (If) ($R_1$=$R_2$=$R_3$=$R_4$=H, $R_5$=4-bromobenzoyl, and X and Y together represent lactone) is obtained. The obtained 2'-monoarylcarbonyl derivatives are, if required, subjected to O-acylation according to the process B1/. Thus, e.g. by reaction with acetic acid anhydride according to the above described process there is obtained triacetate (Ig) ($R_1$=$R_3$=$R_4$=acetyl, $R_2$=$R_5$=4-bromobenzoyl, X and Y together represent lactone). In the case of disubstituted derivatives, together with acylation of 2'-hydroxyl group there simultaneously comes to the acylation of hydroxyl groups on 1-N-[2- or 1N-[4-position of the compound of (Ia). By the O-acylation with at least 5 equivalents of the chlorides of arylcarboxylic acids, preferably 4-bromobenzoyl chloride, at an increased temperature, preferably at a reflux temperature of the reaction mixture, a mixture of dibromobenzoate (Ih) ($R_1$=$R_5$=4-bromobenzoyl, $R_2$=$R_3$=$R_4$=H, X and Y together represent lactone) and (Ii) ($R_3$=$R_5$=4-bromobenzoyl, $R_1$=$R_2$=$R_4$=H, X and Y together represent lactone) is formed which is separated by a chromatography on a silica gel column, preferably using the solvent system $CH_2Cl_2/CH_3OH$, 95:5 and then, if required, subjected to a solvolysis according to the process described above, whereby at deacylation of 2'-esters, preferably of 2'-O-(4-bromobenzoate), monobromobenzoate (Ik) ($R_1$=4-bromobenzoyl, $R_2$=$R_3$=$R_4$=$R_5$=H, X and Y together represent lactone) and (Ij) ($R_3$=4-bromobenzoyl, $R_1$=$R_2$=$R_4$=$R_5$=H, X and Y together represent lactone) respectively are formed.

Transesterification of the compound (Ia) according to C/ is carried out with derivatives of carboxylic acids, preferably with 3 to 5 equimolar excess of ethylene carbonate or 1,1 thiocarbonyldiimidazole with respect to the starting compound (Ia), in a suitable solvent, preferably in aromatic solvents, e.g. benzene, chlorinated hydrocarbons or lower alkylalcanoates, e.g. ethyl acetate, at an increased temperature, preferably at a reflux temperature of the reaction mixture, during 3 to 9 hours, yielding a cyclic carbonate or thiocarbonate ($R_1$ and $R_2$ together represent C=O or C=S groups, $R_3$=$R_4$=$R_5$=H, X and Y together represent lactone).

Reduction of the compound (Ia) according to D/ is carried out with complex metal hydrides, preferably sodium borohydride, in the presence of tertiary alcohols, preferably t-butanol, in an inert solvent, preferably in lower alcohols, preferably methanol, at an increased temperature, preferably at reflux temperature of the reaction mixture, yielding a mixture of isomeric 9-hydroxy-8(R)-(Im) and 9-hydroxy-8 (S)-derivative (In) ($R_1$=$R_2$=$R_3$=$R_4$=$R_5$=H, X is $CH_2OR_6$ (group, wherein $R_6$ is hydrogen, and Y is hydroxyl group) which are, if required, separated by chromatography on a silica gel column and subsequently, if required, subjected to O-acylation according to B1/.

Pharmaceutically acceptable addition salts, which are also an object of the present invention, are obtained by reaction of seco-derivatives of the general formula (I) with an at least equimolar amount of a suitable inorganic or organic acid such as hydrochloric, hydroiodic, sulfuric, phosphoric, acetic, propionic, trifluoroacetic, maleic, citric, stearic, succinic, ethylsuccinic, methanesulfonic, benzenesulfonic, p-toluenesulfonic, laurylsulfonic acid and the like, in a reaction-inert solvent. Addition salts are isolated by filtration if they are insoluble in the reaction-inert solvent, by precipitation by means of non-solvent or by evaporation of the solvent, most frequently by lyophilisation.

By the given series of reactions on 6-deoxy-6,9-epoxy-8 (R)-methyl-10-amino-9,10-seco-erythromycin A of formula (II) there is obtained a series of novel, hitherto undescribed linear derivatives with very reactive terminal functional groups, which opens the possibility for the preparation of a whole series of novel macrolides with modified macrocyclic aglycone. For reasons of simplicity, the position marks of hydrogen and carbon atoms at stating the spectroscopic data of novel secomacrolides in the experimental part of the patent application are the same as these atoms had before the inversion of the C-10/C-15 fragment.

The invention is illustrated by the following examples which do not limit the scope of the invention in any way.

EXAMPLE 1

1-N-(2,3,4-trihydroxy-1,3-dimethyl-hexyl)-amido-10,11,12,13,14,15-hexanor-6-deoxy-6,9-epoxy-9,10-secoerythromycin A (Ia)

Method 1

6-Deoxy-6,9-epoxy-8(R)-methyl-10-amino-9,10-secoerythromycin A (EP 0 735 041 A1, Feb. 10, 1996) (15 g, 0.02 mole) was dissolved in 540 mL of a mixture of acetone-water (1:5) and heated under stirring for 2 hours at a temperature 55–60° C. The reaction mixture was evaporated at reduced pressure, to the water residue $CHCl_3$ (100 mL) was added (pH 7.45) and then, upon alkalizing to pH 9.0 (10% NaOH) layers were separated and the water layer was extracted for two more times with $CHCl_3$ (100 mL). The combined organic extracts were dried over $K_2CO_3$ and evaporated, yielding a solid residue (12.9 g). By means of chromatography on a silica gel column using the solvent system $CHCl_3/CH_3OH/conc.$ $NH_4OH$, 6:1:0.1, from the crude product (2.5 g) a chromatographically homogeneous substance (Ia) (1.48 g) was obtained, with the following physical-chemical constants:

Rf 0.337, $EtAc/(n-C_6H_6)/NHEt_2$, 100:100:20. Rf 0.621, $CH_2Cl_2/CH_3OH/NH_4OH$, 90:9:1.5.

IR ($CHCl_3$) $cm^{-1}$ 3400, 2980, 2950, 1770, 1660, 1540, 1460, 1390, 1270, 1110, 1050, 1005.

$^1H$ NMR (300 MHz, $CDCl_3$) δ: 7.45 (CONH), 4.93 (H-1"), 4.37 (H-1'), 4.19 (H-3), 4.11 (H-10), 3.80 (H-11), 3.65 (H-5), 3.28 (3"-$OCH_3$), 3.20 (H-13), 2.79 (H-8), 2.46 (H-2), 2.27/3'-$N(CH_3)_2$/, 2.20 (H-7a), 2.00 (H-4), 1.98 (H-7b), 1.59 (H-14a), 1.55 (6-$CH_3$), 1.35 (H-14b), 1.28 (8-$CH_3$), 1.26 (10-$CH_3$), 1.14 (12-$CH_3$), 1.11 (2-CH3), 1.09 (4-$CH_3$), 1.05 (15-$CH_3$).

$^{13}C$ NMR (75 MHz, $CDCl_3$) δ:179.4 (C-9), 174.5 (C-1), 105.6 (C-1'), 96.3 (C-1"), 86.4 (C-6), 86.2 (C-5), 83.3 (C-13), 79.5 (C-3), 75.2 (C-11), 74.9 (C-12), 49.3 (3"-$OCH_3$), 48.8 (C-10), 42.6 (C-2), 40.0/3'-$N(CH_3)_2$/, 39.1 (C-7), 38.5 (C-4), 34.2 (C-8), 25.0 (C-14), 23.8 (6-$CH_3$), 21.3 (12-$CH_3$), 15.7 (10-$CH_3$), 14.9 (8-$CH_3$), 11.6 (15-$CH_3$), 11.0 (4-$CH_3$), 9.9 (2-$CH_3$).

EI-MS m/z 748

Method 2

6-Deoxy-6,9-epoxy-8(R)-methyl-10-amino-9,10-secoerythromycin A (EP 0 735 041 A1, Feb. 10, 1996) (1 g, 0.00134 mole) was suspended in 100 mL of water and left standing for 3 hours at room temperature. To the reaction mixture $CHCl_3$ (30 mL) was added and the pH was adjusted with 10% NaOH to 9.0, the layers were separated and the water layer was extracted for two more times with $CHCl_3$ (60 mL). The combined organic extracts were dried over $K_2CO_3$, evaporated on a rotating evaporator and then purified by chromatography on a silica gel column using the solvent system $CHCl_3/CH_3OH/conc.$ $NH_4OH$, 6:1:0.1 as described in Method A.

Example 2

5-O-Desosaminyl-1-N-(2,3,4-trihydroxy-1,3-dimethyl-hexyl)-amido-10,11,12,13,14,1 5-hexanor-6-deoxy-6,9-epoxy-9,10-secoerythromycin A (Ib)

1-N-(2,3,4-trihydroxy-1,3-dimethyl-hexyl)-amido-10,11,12,13,14,15-hexanor-6-deoxy-6,9-epoxy-8(R)-methyl-9,10-secoerythromycin A (Ia) from Example 1 (6 g, 0.008 mole) was dissolved in 300 mL of 0.25 N HCl and then stirred for 2 hours at room temperature. To the reaction mixture $CHCl_3$ (40 mL) (pH 2.0) was added, the layers were separated and the water layer was again extracted twice with $CHCl_3$. After alkalizing to pH 10 (with 20% NaOH), the water solution was extracted again with $CHCl_3$. The combined organic extracts were dried at pH 10 over $K_2CO_3$, filtered and evaporated, yielding a crude product (1.3 g). By chromatography on a silica gel column using the solvent system $CH_2Cl_2/CH_3OH/conc.$ $NH_4OH$, 90:9:1, a chromatographically homogeneous product (Ib) (0.85 g) was obtained with the following physical-chemical constants:

M.p. 87–89° C.

Rf 0.324, $CH_2Cl_2/CH_3OH/NH_4OH$, 90:9:1.5. Rf 0.222, $CHCl_3/CH_3OH$, 7:3.

IR ($CHCl_3$) $cm^{-1}$ 3420, 2980, 2940, 2870, 1740, 1640, 1500, 1480, 1380, 1295, 1230, 1170, 1140, 1120, 980.

Example 3

1-N-(2,3,4-trihydroxy-1,3-dimethyl-hexyl)-amido-10,11,12,13,14,1 5-hexanor-6-deoxy-6,9-epoxy-9,10-secoerythronolide A (Ic)

5-O-Desosaminyl-1-N-(2,3,4-trihydroxy-1,3-dimethyl-hexyl)-amido-10,11,12,13,14,15-hexanor-6-deoxy-6,9-epoxy-8(R)-methyl-9,10-secoerythromycin A (Ib) from Example 2 (4 g, 0.0068 mole) was dissolved in 20 mL of $CHCl_3$, 2N HCl (40 mL) was added and then the reaction mixture was stirred at reflux for 2 hours. After cooling to the room temperature, $CHCl_3$ was separated and the water layer was again extracted twice with $CHCl_3$ (25 mL). The water solution was evaporated at a reduced pressure, to the solid residue $CH_3OH$ (40 mL) was added and the reaction suspension was stirred for 1 hour at room temperature, filtered and the clear filtrate was evaporated on a rotating evaporator yielding a solid residue (3 g). By chromatography on a silica gel column using the solvent system $CHCl_3/CH_3OH$, 7:3, from the crude product (0.6 g) a chromatographically homogeneous substance (Ic)) (0.28 g) was obtained with the following physical-chemical constants:

Rf 0.793, $CHCl_3/CH_3OH$, 7:3.

IR ($CHCl_3$) $cm^{-1}$ 3420, 2980, 2940, 2890, 1760, 1615, 1550, 1460, 1390, 1300, 1240, 1160, 1100, 970.

¹H NMR (300 MHz, Py-d₅) δ: 8.84 (CONH), 4.85 (H-10), 4.44 (H-3), 4.41 (H-11), 4.01 (H-5), 4.00 (H-13), 3.06 (H-2), 2.81 (H-8), 2.41 (H-4), 2.30 (H-7a), 2.10 (H7b), 2.03 (H-14a), 1.72 (H-14b), 1.60 (2-CH₃), 1.59 (10-CH₃), 1.55 (12-CH₃), 1.46 (4-CH₃), 1.44 (6-CH₃), 1.21 (8-CH₃), 1.17 (15-CH₃).

¹³C NMR (75 MHz, Py-d₅) δ: 179.4 (C-9), 174.4 (C-1), 86.5 (C-6), 79.2 (C-S), 79.2 (C-13), 77.8 (C-3), 77.1 (C-11), 75.6 (C-12), 47.0 (C-10), 44.9 (C-2) 39.3 (C-7), 36.6 (C-4), 34.5 (C-8), 24.9 (C-14), 22.0 (6-CH₃), 20.0 (12-CH₃), 15.3 (10-CH₃), 15.5 (8-CH₃), 12.1 (15-CH₃), 8.2 (4-CH₃), 16.3 (2-CH₃).

EI-MS m/z 432

Example 4

2',4"-O-diacetyl-1-N-(2,4-O-diacetyl-3-hydroxy-1,3-dimethyl-hexyl)-amido-10,11,12,13,14,1 5-hexanor-6-deoxy-6,9-epoxy-9,10-secoerythromycin A (Id)

To a solution of the substance (Ia) (3.38 g, 0.0045 mole) from Example 1 in pyridine (40 mL), acetic acid anhydride (12 mL) was added and then the reaction mixture was left standing for 3 days at room temperature. The solution was poured on a mixture of water and ice (pH 4.8), the pH of the mixture was adjusted with 10% NaOH to 9.0 and the obtained product was extracted with $CHCl_3$. The combined organic extracts were dried over $K_2CO_3$, filtered and evaporated, yielding a crude product (4.15 g). By chromatography on a silica gel column using the system $CH_2Cl_2$/$CH_3OH$/conc. $NH_4OH$, 90:9:1.5, from the product (1.2 g) a chromatographically homogeneous tetraacetate (Id) (0.65 g) was obtained with the following physical-chemical constants:

Rf 0.662, EtAc/(n-$C_6H_6$)/NHEt₂, 100:100:20.

IR($CHCl_3$)cm⁻¹ 1745, 1720, 1650, 1515, 1450, 1370, 1240, 1165, 1110, 1060.

¹H NMR (300 MHz, CDCl₃) δ: 6.87 (CONH), 4.86 (H-11), 4.86 (H-1"), 4.51 (H-2'), 4.81 (H-13), 4.66 (H-4"), 4.51 (H-1'), 4.43 (H-10), 3.95 (H-3), 3.75 (H-5), 3.37 (3"-OCH₃), 2.75 (H-8), 2.23 (H-2), 2.29/3'-N(CH₃)₂/, 2.16 (H-7a), 2.15, 2.07, 2.05 and 2.03 (COCH₃), 1.90 (H-7b), 1.84 (H-14a), 1.66 (H-4), 1.58 (6-CH₃), 1.56 (H-14b), 1.29 (12-CH₃), 1.25 (8-CH₃), 1.23 (5'-CH₃), 1.21 (10-CH₃), 1.12 (2-CH₃), 1.11 (3"-CH₃), 1.11 (5"-CH₃), 106 (4-CH₃), 0.90 (15-CH₃).

¹³C NMR (75 MHz, CDCl₃) δ: 179.8 (C-9), 173.7 (C-1), 170.3, 170.3, 170.1 and 169.6 (COCH₃), 101.0 (C-1'), 96.2 (C-1"), 85.5 (C-6), 81.5 (C-5), 78.6 (C-4"), 78.1 (C-3), 76.8 (C-13), 76.0 (C-11), 74.9 (C-12), 62.7 (C-3'), 62.3 (C-5"), 49.4 (3"-OCH₃), 45.1 (C-10), 44.7 (C-2), 40.3/3'-N(CH₃)₂/, 39.8 (C-7), 39.8 (C-4), 33.3 (C-8), 30.6 (C-4'), 24.7 (6-CH₃), 21.9 (C-14), 21.0, 20.7, 20.6, 20.5 (COCH₃), 20.9 (3"-CH₃), 20.7 (5'-CH₃), 18.4 (12-CH₃), 17.2 (5"-CH₃), 16.0 (10-CH₃), 14.5 (8-CH₃), 11.3 (4-CH₃), 10.7 (15-CH₃), 10.5 (2-CH₃).

EI-MS m/z 916.

Example 5

4"-O-acetyl-1-N-(2,4-O-diacetyl-3-hidroxy-1,3-dimethyl-hexyl)-amido-10,11,12,13,14,15-hexanor-6-deoxy-6,9-epoxy-9,10-secoerythromycin A (Ie)

A solution of the substance (Id) (2 g, 0.00218 mole) from Example 4 in CH₃OH (50 mL) was left standing for 3 days at room temperature. By evaporation at a reduced pressure the reaction mixture was concentrated to about ¼ of the volume, water (100 mL) (pH 6.9) was added and then the obtained product was isolated by extraction with $CH_2Cl_2$ at pH 9.0 (10% NaOH). The combined organic extracts were dried over $K_2CO_3$, filtered and evaporated, yielding a crude product (1.72 ). By chromatography on a silica gel column using the solvent system $CH_2Cl_2$/$CH_3OH$, 85:15, a chromatographically homogeneous triacetate (Ie) (0.85 g) was obtained with the following physical-chemical constants:

Rf 0.582, EtAc/(n-$C_6H_6$)/NHEt₂, 100:100:20.

IR(CHCl3) cm⁻¹ 1740, 1710, 1665, 1515, 1460, 1380, 1240, 1170, 1130, 1060.

¹H NMR (300 MHz, CDCl₃) δ: 7.14 (CONH), 4.87 (H-13), 4.85 (H-1"), 4.77 (H-11), 4.65 (H-4"), 4.47 (H-10), 4.41 (H-1'), 4.37 (C-5"), 4.07 (H-3), 3.75 (H-5), 3.33 (3"-OCH₃), 3.26 (H-2'), 2.75 (H-8), 2.50 (H-2), 2.32/3'-N(CH₃)₂/, 2.13, 2.06, and 2.03 (COCH₃), 9.09 (H-7a), 1.91 (H-4), 1.83 (H-14a), 1.58 (6-CH₃), 1.54 (H-14b), 1.29 (12-CH₃), 1.26 (8-CH₃), 1 .23 (5'-CH₃), 1.18 (10-CH₃), 1.15 (4-CH₃), 1.12 (2-CH₃), 1.10 (3"-CH₃), 1.08 (5"-CH₃), 0.90 (H-15).

¹³C NMR (75 MHz, CDCl₃) δ: 179.1 (C-9), 173.8 (C-1), 170.4, 170.1 and 170.1 (COCH₃), 103.4 (C-1'), 96.0 (C-1"), 85.6 (C-6), 79.4 (C-3), 82.8 (C-5), 78.2 (C-11), 75.5 (C-13), 74.5 (C-12), 69.9 (C-2'), 65.0 (C-3'), 62.1 (C-5"), 49.1 (3"-OCH₃), 44.5 (C-10), 42.6 (C-2), 39.7/3'-N(CH₃)₂/, 38.1 (C-7), 38.5 (C-4), 33.4 (C-8), 23.7 (6-CH₃), 21.5 (C-14), 20.5, 20.3 and 20.2 (COCH₃), 20.6 (3"-CH₃ and 5'-CH₃), 18.1 (12-CH₃), 16.7 (5"-CH₃), 16.2 (4-CH₃), 14.3 (8-CH₃), 11.2 ( 10-CH₃), 10.9 (2-CH₃), 10.4 (C-15).

EI-MS m/z 874.

Example 6

2'-O-(4-Bromobenzoyl)-1-N-(2,3,4-trihydroxy-1,3-dimethyl-hexyl)-amido-10,11,12,13,14,15-hexanor-6-deoxy-6,9-epoxy-9,10-secoerythromycin A (If)

The substance (Ia) (2.0 g, 0.0027 mole) from Example 1 was dissolved in dry acetone (10 mL), NaHCO₃ (0.4 g, 0.00476 mole) was added and then under stirring over 1 hour, at 0–5 ° C. a solution of 4-bromobenzoyl chloride (0.83 g, 0.0038 mole) in acetone (10 mL) was added dropwise. The reaction mixture was stirred for further 3 hours at the same temperature, filtered, acetone was evaporated by distillation at a reduced pressure and to the obtained residue water (30 mL) was added, whereupon by extraction with CHCl₃ at pH 8.5 a product was isolated. After drying over $K_2CO_3$ and evaporation of the combined organic extracts a crude product (2.3 g) was isolated. By chromatography on a silica gel column using the solvent system CHCl₃/CH₃OH/conc. NH₄OH, 90:9:1.5, a chromatographically homogeneous 2'-(p-bromobenzoyl)-derivative (If) (1.23 g) was obtained with the following physical-chemical constants:

Rf 0.390, EtAc/(n-$C_6H_6$)/NHEt₂, 100:100:20. Rf 0.814, $CH_2Cl_2$/CH₃OH/NH₄OH, 90:9:1.5.

IR (CHCl₃) cm⁻¹ 1740, 1710, 1650, 1580, 1500, 1450, 1390, 1370, 1340, 1265, 1165, 1160, 1120, 1100, 1055, 1010.

¹H NMR (300 MHz, CDCl₃) δ: 7.73 (Ph), 6.61 (CONH), 5.04 (H-2'), 4.86 (H-1"), 4.61 (H-1'), 4.02 (H-10), 3.98 (H-5"), 3.92(H-3), 3.82 (H-11), 3.73 (H-5), 3.59 (H-5'), 3.36 (3"-OCH₃), 3.26 (H-3'), 3.25 (H-13), 3.03 (H-4"), 2.87 (H-3'), 2.77 (H-8), 2.37 (H-9"), 2.30/3'-N(CH₃)₂/, 2.20 (H-7a), 2.16 (H-9), 1.84 (H-4'a), 1.78 (H-7b), 1.56 (H-14a), 1.59 (6-CH₃), 1.56 (H-4), 1.41 (H-14b), 1.27 (10-CH₃), 1.57

(6-CH$_3$), 1.23 (8-CH$_3$), 1.13 (12-CH$_3$), 0.83 (4-CH$_3$), 1.05 (2-CH$_3$), 1.04 (C-15).

$^{13}$C NMR (75 MHz, CDCl$_3$) δ: 180.6 (C-9), 175.6 (C-1), 164.7 (COBr), 131.7, 131.3, 129.2 and 128.1 (aryl), 101.1 (C-1'), 94.8 (C-1"), 86.1 (C-6), 79.9 (C-3), 82.2 (C-5), 81.2 (C-13), 78.0 (C-3), 75.9 (C-11), 74.3 (C-12), 73.0 (C-3"), 72.2 (C-2'), 65.4 (C-5"), 63.5 (C-3'), 49.6 (3"-OCH$_3$), 48.1 (C-10), 45.3 (C-2), 41.7 (C-4), 40.2/3'-N(CH$_3$)$_2$/, 37.0 (C-7), 34.8 (C-2"), 33.8 (C-8), 31.1 (C-4'), 25.3 (6-CH$_3$), 24.9 (C-14), 21.7 (12-CH$_3$), 18.1 (5"-CH$_3$), 13.8 (10-CH$_3$), 14.7 (8-CH$_3$), 11.8 (4-CH$_3$), 11.1 (C-15), 10.0 (2-CH$_3$).

EI-MS m/z 931.

Example 7

2'-O-(4-Bromobenzoyl)-4"-O-acetyl-1-N-(2,4-O-diacetyl-3-hidroxy-1,3-dimethyl-hexyl)-amido-10, 11,12,13,14,15-hexanor-6-deoxy-6,9-epoxy-9,10-seco-erythromycin A (Ig)

To a solution of the substance (If) (0.50 g, 0.00054 mole) from Example 6 in pyridine (10 mL) acetic acid ahydride (2.5 mL) was added and then the reactiom mixture was left standing for 3 days at room temperature. The solution was poured on a mixture of water and ice, the pH was adjusted with 10% NaOH to 9.0 and the obtained product was isolated by extraction with CHCl$_3$. The combined organic extracts were dried over K$_2$CO$_3$, filtered and evaporated at a reduced pressure yielding a crude product (0.57 g). By chromatography on a silica gel column using the system CH$_2$Cl$_2$/CH$_3$OH/conc. NH$_4$OH, 90:9:1.5, from the obtained precipitate (1.2 g) a chromatographically homogeneous substance (Ig) (0.18 g) was obtained with the following physical-chemical constants:

Rf 0.773, EtAc/(n-C$_6$H$_6$)/NHEt$_2$, 100:100:20. Rf 0.938, CH$_2$Cl$_2$/CH$_3$OH/NH$_4$OH, 90:9:1.5.

IR (CHCl$_3$) cm$^{-1}$ 3340, 2970, 1740, 1710, 1650, 1580, 1515, 1450, 1370, 1240, 1160, 1130, 1100, 1040, 1010.

$^1$H NMR (300 MHz, CDCl$_3$) δ: 7.73 (Ph), 6.83 (CONH), 3.38 (3"-OCH$_3$), 2.28/3'-N(CH$_3$)$_2$/, 2.17, 2.03 and 2.02 (COCH$_3$).

Example 8

2'-O-(4-Bromobenzoyl)-1-N-2-(4-bromobenzoyl)-3, 4-dihydroxy-1,3-dimethyl-hexyl]-amido-10,11,12, 13,14,15-hexanor-6-deoxy-6,9-epoxy-9,10-seco-erythromycin A (Ih) and 2'-O-(4-bromobenzoyl)-1-N-[4-(4-bromobenzoyl)-2, 3-dihydroxy-1,3-dimethyl-hexyl]-amido-10,11,12, 13,14,15-hexanor-6-deoxy-6,9-epoxy-9,10-seco-erythromycin A (Ii)

The substance (Ia) (7.8 g, 0.0104 mole) from Example 1 was dissolved in dry acetone (200 mL) and NaHCO$_3$ (23.55 g, 0.280 mole) was added and then the reaction suspension was heated under stirring to the reflux temperature. Under stirring over 30 minutes a solution of 4-bromobenzoyl chloride (11.45 g, 0.052 mole) in acetone (80 mL) was added dropwise, the reaction suspension was stirred under reflux for further 30 hours, cooled to room temperature, filtered and evaporated at a reduced pressure. The obtained precipitate was dissolved in CH$_2$Cl$_2$ (100 mL), water (60 mL) was added, whereupon by extraction with CHCl$_3$ at pH 9.0 a product was isolated. The combined organic extracts were washed with a saturated NaHCO$_3$ solution (80 mL) and water (40 mL) and dried over K$_2$CO$_3$. After evaporation of the solvent, a mixture (12.0 g) of dibromobenzoate (Ih) and (Ii) was obtained, which was separated by chromatography on a silica gel column using the solvent system CH$_2$Cl$_2$/CH$_3$OH, 95:5, yielding chromatographically homogeneous title products (Ih) and (Ii) with the following physical-chemical constants:

Substance (Ih):

Rf 0.539, CH$_2$Cl$_2$/CH$_3$OH/NH$_4$OH, 90:9:0.5.

IR (CHCl$_3$) cm$^{-1}$ 1755, 1720, 1660, 1590, 1520, 1490, 1450, 1390, 1370, 1340, 1270, 1165, 1160, 1120, 1100, 1060, 1015, 850.

$^1$H NMR (300 MHz, CDCl$_3$) δ: 7.72 (Ph), 7.00 (CONH), 5.27 (H-11), 4.96 (H-2'), 4.72 (H-1"), 4.56 (H-1'), 4.53 (H-10), 3.93 (H-5"), 3.77 (H-3), 3.65 (H-5), 3.13 (H-13), 3.57 (H-5'), 3.25 (3"-OCH$_3$), 3.05 (H-4"), 2.78 (H-3'), 2.42 (H-2"), 2.34 (H-8 ), 2.24/3'N(CH$_3$)$_2$/, 2.02 (H-7a), 2.05 (H-2), 2.04 (H-2"a), 1.81 (H-4'a), 1.77 (H-7b), 1.71 (H-14a), 1.51 (H-2"b), 1.41 (H-14b), 1.50 (H-4), 1.41 (H-4'b), 1.36 (10-CH$_3$), 1.27 (12-CH$_3$), 1.30 (5"-CH$_3$), 1.28 (5'-CH$_3$), 1.24 (6-CH$_3$), 1.23 (3"-CH$_3$), 1.14 (8-CH$_3$), 1.01 (2-CH$_3$), 0.98 (H-15), 0.83 (4-CH$_3$), 0.80 (H-2"b).

$^{13}$C NMR (75 MHz, CDCl$_3$) δ: 180.3 (C-9), 174.6 (C-1), 166.4 and 164.5 (COBr), 131.6, 131.5, 129.1, 128.5, 128.2, 127.8 (Ph), 101.1 (C-1'), 96.3 (C-1"), 85.5 (C-6), 81.5 (C-5), 79.3 (C-11), 78.1 (C-3), 77.8 (C-4"), 77.0 (C-13), 75.7 (C-12), 72.6 (C-3"), 72.0 (C-2'), 68.9 (C-5'), 64.9 (C-5"), 63.0 (C-3'), 49.2 (3"-OCH$_3$), 45.3 (C-10), 45.3 (C-2), 40.6 (C-4), 40.6/3'N(CH$_3$)$_2$/, 36.9 (C-7), 33.1 (C-8), 34.5 (C-2"), 30.7 (C-4'), 24.3 (6-CH$_3$), 22.6 (C-14), 21.3 (3"-CH$_3$), 20.6 (5'-CH$_3$), 17.8 (5"-CH$_3$), 17.7 (12-CH$_3$), 15.3 (10-CH$_3$), 14.2 (8-CH$_3$), 11.5 (4-CH$_3$), 11.3 (C-15), 10.0 (2-CH$_3$).

Substance (Ii):

Rf 0.744, CH$_2$Cl$_2$/CH$_3$OH/NH$_4$OH, 90:9:0.5

IR (CHCl$_3$) cm$^{-1}$ 3450, 2980, 2940, 1770, 1730, 1650, 1600, 1540, 1495, 1460, 1405, 1390, 1350, 1280,1170, 1110, 1070, 1015, 850.

$^1$H NMR (300 MHz, CDCl$_3$) δ: 7.72 (Ph), 6.51 ,CONH), 5.13 (H-13), 5.00 (H-2'), 4.55 (H-2'), 4.52 (H-1"), 4.09 (H-10), 3.92 (H-3'), 3.85 (H-5"), 3.68 (H-5), 3.65 (H-11), 3.54 (H-5'), 3.28 (3'-OCH$_3$), 3.00 (H-4"), 2.79 (H-3'), 2.69 (H-8), 2.25/3'N(CH$_3$)$_2$/, 2.16 (H-7a), 2.10 (H-2), 2.04 (H-2"a), 2.00 (H-14a), 1.80 (H-4'a), 1.76 (H-7b), 1.62 (H-14b), 1.53 (H-4), 1.44 (H-4'b), 1.27 (5"-CH$_3$), 1.27 (5'-CH$_3$), 1.14(3"-CH$_3$), 1.04 (H-15), 0.80 (H-2"b).

$_{13}$C NMR (75 MHz, CDCl$_3$) δ: 180.1 (C-9), 174.9 (C-1), 165.8 and 164.7 (COBr), 131.8, 131.6, 131.5, 131.2, 131.0, 129.3, 129.1, 127.9 (Ph), 101.2 (C-1'), 94.1 (C-1"), 85.5 (C-6), 81.4 (C-5), 76.9 (C-3), 77.2 (C-4"), 78.3 (C-13), 74.6 (C-12), 72.6 (C-3"), 71.9 (C-2'), 70.2 (C-11), 69.0 (C-5'), 65.2 (C-5"), 63.3 (C-3'), 49.2 (3"-OCH$_3$), 46.7 (C-10), 44.8 (C-2), 41.5 (C-4), 40.5/3'N(CH$_3$)$_2$/, 36.9 (C-7), 33.3 (C-8), 33.2 (C-2"), 30.8 (C-4'), 25.0 (6-CH$_3$), 21.7 (C-14), 21.3 (3"-CH$_3$), 20.8 (5'-CH$_3$), 17.5 (5"-CH$_3$), 16.3 (12-CH$_3$), 14.4 (8-CH$_3$), 13.5 (10-CH$_3$), 11.1 (C-15), 10.7 (4-CH$_3$), 9.8 (2-CH$_3$).

Example 9

1-N-[2,3-dihydroxy-4-(4-bromobenzoyl)-1,3-dimethyl-hexyl]-amido-10,11,12,13,14,15-hexanor-6-deoxy-6,9-epoxy-9,10-secoerythromycin A (Ij)

The product (Ii) (4.6 g) from Example 8 was dissolved in methanol (50 mL), water (10 mL) was added and then the reaction solution was left standing for 24 hours at room temperature. By evaporation at a reduced pressure methanol was evaporated, to the oily residue water (20 mL) was added and by extraction with CHCl$_3$ at pH 9.0 a product was isolated. After drying over K$_2$CO$_3$ and evaporation of the combined organic extracts, a crude product (4.1 g) was obtained. By chromatography on a silica gel column using the solvent system CH$_2$Cl$_2$/CH$_3$OH/conc. NH$_4$OH, 90:9:0.5, from the crude product (1.90 g) a TLC homogeneous monobromobenzoate (Ij) (0.72 g) was isolated wih the following physical-chemical constants:

Rf 0.391, CH$_2$Cl$_2$/CH$_3$OH/NH$_4$OH, 90:9:0.5.

IR (CHCl$_3$) cm$^{-1}$ 3400, 2980, 2950, 1770, 1660, 1540, 1460, 1390, 1270, 1110, 1050, 1005.

$^1$H NMR (300 MHz, CDCl$_3$) δ: 7.72 (aryl), 7.26 (CONH), 5.13 (H-13), 4.54 (H-1"), 4.36 (H-1'), 4.20 (H-10), 4.14 (H-3), 3.87 (H-5"), 3.70 (H-5), 3.57 (H-5'), 3.54 (H-11), 3.29 (H-2'), 3.19 (3"-OCH$_3$), 2.94 (H-4"), 2.53 (H-8), 2.53 (H-2), 2.45 (H-3'), 2.30/3'N(CH$_3$)$_2$/, 2.15 (H-7a), 2.02 (H-14a), 2.00 (H-7b), 1.98 (H-2"a), 1.86 (H-4), 1.69 (H-4'a), 1.61 (H-14b), 1.50 (6-CH$_3$), 1.33 (H-4'b), 1.29 (12-CH$_3$), 1.26 (5'-CH$_3$), 1.27 (3"-CH$_3$), 1.26 (8-CH$_3$), 1.25 (5"-CH$_3$), 1.20 (10-CH$_3$), 1.10 (3"-CH$_3$), 1.02 (2-CH$_3$), 0.99 (4-CH$_3$), 0.92 (H-15), 0.88 (H-2"b).

$^{13}$C NMR (75 MHz, CDCl$_3$) δ: 179.3 (C-9), 174.4 (C-1), 165.9 (COBr), 131.8, 131.1, 129.0 and 128.1 (aryl), 104.9 (C-1'), 94.6 (C-1"), 86.1 (C-6), 84.5 (C-5), 76.9 (C-3), 78.1 (C-13), 74.6 (C-12), 70.5 (C-11), 70.2 (C-2'), 65.3 (C-5"), 65.8 (C-3'), 49.0 (3"-OCH$_3$), 46.1 (C-10), 41.6 (C-2), 41.0/3'N(CH$_3$)$_2$/, 39.1 (C-4), 38.7 (C-7), 33.9 (C-2"), 33.8 (C-8), 27.8 (C-4'), 21.6 (C-14), 23.6 (6-CH$_3$), 20.9 (5'-CH$_3$), 21.2 (3"-CH$_3$), 17.2 (5"-CH$_3$), 16.2 (12-CH$_3$), 14.5 (8-CH$_3$), 13.6 (10-CH$_3$), 9.9 (2-CH$_3$), 10.6 (4-CH$_3$), 10.9 (C-15).

Example 10

1-N-(2-(4-bromobenzoyl)-3,4-dihydroxy-1,3-dimethyl-hexyl]-amido-10,11,12,13,14,15-hexanor-6-deoxy-6,9-epoxy-9,10-secoerythromycin A (Ik)

From the product (Ih) (2.20 g) from Example 8, according to the process in Example 9, after purification of the crude product by chromatography on a silica gel column and evaporation of the fractions with Rf 0.283, a chromatographically homogeneous title product (Ik) (0.95 g) was obtained.

Rf 0.283, CH$_2$Cl$_2$/CH$_3$OH/NH$_4$OH, 90:9:0.5.

$^1$H NMR (300 MHz, CDCl$_3$) δ: 7.72 (Ph), 7.00 (CONH), 5.20 (H-11), 4.72 (H-1"), 4.36 (H-1'), 4.53 (H-10), 3.93 (H-5"), 3.77 (H-3), 3.65 (H-5), 3.23 (H-13), 3.59 (H-5'), 3.36 (H-2'), 3.25 (3"-OCH$_3$), 3.05 (H-4"), 2.72 (H-3'), 2.42 (H-2"), 2.34 (H-8), 2.28/3'N(CH$_3$)$_2$/, 2.02 (H-7a), 2.05 (H-2), 2.04 (H-2"a), 1.71 (H-4'a), 1.77 (H-7b), 1.71 (H-14a), 1.51 (H-2"b), 1.41 (H-14b), 1.50 (H-4), 1.26(H-4'b), 1.36 (10-CH$_3$), 1.27 (12-CH$_3$), 1.26 (5"-CH$_3$), 1.26 (5'-CH$_3$), 1.64 (6-CH$_3$), 1.20 (3"-CH$_3$), 1.14 (8-CH$_3$), 1.01 (2-CH$_3$), 0.98 (H-15), 0.83 (4-CH$_3$), 0.80 (H-2"b).

Example 11

1-N-[4-hydroxy-1,3-dimethyl-hexyl]-amido-10,11,12,13,14,15-hexanor-6-deoxy-6,9-epoxy-9,10-secoerythromycin A 2,3-cyclic carbonate (Il)

The substance (Ia) from Example 1 (10.0 g, 0.0134 mole) was dissolved in dry benzene (100 mL) and ethylene carbonate (5.0 g, 0.057 mole) was added and then, after dissolving the reagent, K$_2$CO$_3$ (2.0 g, 0.0145 mole) was added. The reaction suspension was refluxed under stiffing for 9 hours, left standing overnight and evaporated at reduced pressure yielding a crude product (Il) (11.0 g). By chromatography on a silica gel column using the solvent system CH$_2$Cl$_2$/CH$_3$OH/conc. NH$_4$OH, 90:9:1.5, from the crude product (3.0 g) a chromatographically homogeneous substance (Il) (1.25 g) was isolated with the following physical-chemical constants:

IR (CHCl$_3$) cm$^{-1}$ 3540, 3300, 1790, 1760, 1660, 1530, 1450, 1380, 1300, 1280, 1230, 1165, 1000.

$^1$H NMR (300 MHz, Py) δ: 8.46 (CONH), 5.26 (H-11), 5.18 (H-1"), 4.81 (H-1'), 4.61 (H-10), 4.54 (H-3), 4.52 (H-5"), 4.19 (H-5), 3.79 (H-13), 3.76 (H-5'), 3.60 (H-2'), 3.41 (3"-OCH$_3$), 3.29 (H-4"), 3.07 (H-2), 2.88 (H-8), 2.61 (H-3'), 255 (H-7a), 2.50 (H-2"a), 2.50 (H-4), 2.24/3'N(CH$_3$)$_2$/, 2.20 (H-7b), 2.24 (H-4'a), 1.75 (6-CH$_3$), 1.73 (H-14a), 1.65 (3"-CH$_3$), 1.65 (3"-CH$_3$), 1.58 (H-2"b), 1.55 (4-CH$_3$), 1.55 (5"-CH$_3$), 1.41 (10-CH$_3$), 1.43 (2-CH$_3$), 1.33 (12-CH$_3$), 1.30 (8-CH$_3$), 1.28 (5'-CH$_3$), 1.16 (H-4'b), 1.16 (H-15).

$^{13}$C NMR (75 MHz, Py) δ: 180.1 (C-9), 175.9 (C-1), 155.0 (CO carbonate), 105.2 (C-1'), 97.7 (C-1"), 88.9 (C-12), 87.1 (C-6), 83.0 (C-5), 82.2 (C-13), 80.8 (C-11), 79.1 (C-3), 70.2 (C-2'), 66.5 (C-5"), 66.2 (C-3'), 50.0 (3"-OCH$_3$), 46.1 (C-10), 44.8 (C-2), 41.0/3'N(CH$_3$)$_2$/, 40.5 (C-4), 39.3 (C-7), 36.4 (C-2"), 34.9 (C-8), 30.9 (C-4'), 25.2 (6-CH$_3$), 24.6 (C-14), 22.1 (5'-CH$_3$), 21.9 (3"-CH$_3$), 19.3 (5"-CH$_3$), 17.2 (12-CH$_3$), 16.8 (2-CH$_3$), 15.7 (10-CH$_3$), 13.9 (8-CH$_3$), 11.3 (4-CH$_3$), 11.6 (C-15).

EI-MS m/z 774.

Example 12

1-N-[2,3,4-trihydroxy-1,3-dimethyl-hexyl]-amido-10,11,12,13,14,15-hexanor-9-deoxo-9-hidroxy-8(R)-methyl-9,10-secoerythromycin A (Im) and 1-N-[2,3,4-trihydroxy-1,3-dimethyl-hexyl]-amido-10,11,12,13,14,15-hexanor-9-deoxo-9-hydroxy-8(S)-methyl-9,10-secoerythromycin A (In)

Into a refluxing solution of the substance (Ia) from Example 1 (3.0 g, 0.004 mole) and NaBH$_4$ (2.4 g, 0.063 mole) in t-butanol (32 mL), under stirring for 5 hours methanol (32 mL) was added dropwise and it was refluxed for further 2 hours. To the cooled mixture water (15 mL) was added and then extracted with CH$_2$Cl$_2$ at pH 2.5. The combined organic extracts were dried over K$_2$CO$_3$, filtered and evaporated at reduced pressure. The crude product (2.4 g) was purified by chromatography on a silica gel column using the solvent system CHCl$_3$/CH$_3$OH/conc. NH$_4$OH, 6:1:0.1. By combining and evaporating the fractions with higher Rf (0.600) with respect to the starting 6,9-lactone (Ia) (Rf 0.553), a mixture (0.45 g) of isomeric products (Im) and (In) was obtained. The isomers were separated by rechromatography on a silica gel column using the system EtAc/(n-C$_6$H$_6$)/Et$_2$NH, 100:100:20. By evaporation of the combined fractions with Rf 0.158 the isomer (Im) (0.2 g) was obtained and by evaporation of the fractions with Rf 0.197 the isomer (In) (0.05 g) was obtained.

Substance (Im):

IR (CHCl$_3$) cm$^{-1}$ 3660, 3600, 3350, 2980, 2930, 1755, 1655, 1515, 1450, 1380, 1150, 1100.

$^1$H NMR (300 MHz, CDCl$_3$) δ: 7.57 (CONH), 4.97 (H-1"), 4.36 (H-1'), 4.17 (H-10), 4.23 (H-3), 4.04 (H-5"), 3.76 (H-11), 3.70 (H-5'), 3.60 (H-9a), 3.46 (H-2'), 3.41 (H-5), 3.28 (3"-OCH$_3$), 3.27 (H-9b), 3.19 (H-13), 2.93 (H-4"), 2.77 (H-3'), 2.50 (H-2), 2.38 (H-2"a), 2.30/3'N(CH$_3$)$_2$/, 2.09 (H-8), 1.95 (H-4), 1.78 (H-4'a), 1.57 (H-14a), 1.40 (H-7b), 1.40 (H-2"b), 1.36 (H-4'b), 1.36 (H-14b), 1.33 (6-CH$_3$), 1.28 (5'-CH$_3$), 1.25 (10-CH$_3$), 1.23 (5"-CH$_3$), 1.18

(3"-CH$_3$), 1.14 (12-CH$_3$), 1.09 (2-CH$_3$), 1.06 (4-CH$_3$), 1.05 (H-15), 0.95 (8-CH$_3$).

$^{13}$C NMR (75 MHz, CDCl$_3$) δ 173.4 (C-1), 106.7 (C-1'), 96.4 (C-1"), 92.5 (C-5), 83.7 (C-13), 80.1 (C-3), 75.0 (C-6), 74.7 (C-11), 74.6 (C-12), 70.2 (C-2'), 69.0 (C-9), 65.4 (C-5"), 64.1 (C-3'), 50.0 (3"-OCH$_3$), 49.0 (C-10), 44.1 (C-7), 41.3 (C-2), 39.5/3'N(CH$_3$)$_2$/, 37.4 (C-4), 34.8 (C-2"), 31.0 (C-8), 27.8 (C-4'), 24.7 (C-14), 22.1 (6-CH$_3$), 21.4 (12-CH$_3$), 20.7 (5'-CH$_3$), 21.1 (3"-CH$_3$), 20.0 (8-CH$_3$), 17.3 (5"-CH$_3$), 16.0 (10-CH$_3$), 10.1 (4-CH$_3$), 11.3 (C-15), 8.4 (2-CH$_3$).

Substance (In):

$^1$H NMR (300 MHz, CDCl$_3$) δ 7.63 (CONH), 5.05 (H-1"), 4.34 (H-1'), 4.22 (H-10), 4.25 (H-3), 4.06 (H-5"), 3.74 (H-11), 3.71 (H-5'), 3.48 (H-9a), 3.34 (H-2'), 3.70 (H-5), 3.28 (3"-OCH$_3$), 3.29 (H-9b), 3.14 (H-13), 2.93 (H-4"), 2.84 (H-3'), 2.50 (H-2), 2.32 (H-2"a), 2.28/3'N(CH$_3$)$_2$/, 1.74 (H-8), 1.93 (H-4), 1.76 (H-4'a), 1.56 (H-14a), 1.74 (H-7a), 1.64 (H-7b), 1.41 (H-2"b), 1.32 (H-4'b), 1.36 (H-14b), 1.34 (6-CH$_3$), 1.27 (5'-CH$_3$), 1.25 (10-CH$_3$), 1.23 (5"-CH$_3$), 1.17 (3"-CH$_3$), 1.15 (12-CH$_3$), 1.11 (2-CH$_3$), 1.07 (4-CH$_3$), 1.46 (H-15), 0.89 (8-CH$_3$).

$^{13}$C NMR (75 MHz, CDCl$_3$) δ 173.6 (C-1), 107.3 (C-1'), 96.3 (C-1"), 91.2 (C-5), 84.5 (C-13), 78.9 (C-3), 75.5 (C-6), 75.1 (C-11), 74.8 (C-12), 70.5 (C-2'), 69.4 (C-9), 65.7 (C-5"), 63.4 (C-3'), 49.3 (3"-OCH$_3$), 49.7 (C-10), 46.7 (C-7), 41.9 (C-2), 39.3/3'N(CH$_3$)$_2$/, 37.4 (C-4), 34.7 (C-2"), 32.0 (C-8), 27.8 (C-4'), 26.2 (6-CH$_3$), 94.9 (C-14), 21.9 (12-CH$_3$), 21.1 (3"-CH$_3$), 20.7 (5'-CH$_3$), 19.6 (8-CH$_3$), 17.4 (5"-CH$_3$), 16.7 (10-CH$_3$), 11.4 (C-15), 10.1 (4-CH$_3$), 8.1 (2-CH$_3$).

Example 13

2',4"-O-Diacetyl-1-N-[2,4-O-diacetyl-3-hidroxy-1,3-dimethyl-hexyl]-amido-10,11,12,13,14,15-hexanor-9-deoxo-9-O-acetyl-8(R)-metyl-9,10-secoerythromycin A (Io)

The substance (Im) (0.70 g) from Example 12 was dissolved in pyridine (10 mL) acetic acid anhydride (5 mL) was added and it was left standing for 2 days at room temperature. The reaction mixture was poured on ice (50 mL) and extracted with CHCl$_3$ at pH 5 and pH 9. Drying over K$_2$CO$_3$ and evaporation of the combined organic extracts at pH 9 gave a crude product (0.87 g), which was suspended in petroleum ether, stirred for 30 minutes at 0–5° C., filtered and dried in a vacuum dryer at 50° C., yielding the chromatographically homogeneous title product (Io) (0.61 g).

Rf 0.473 EtAc/(n-C$_6$H$_6$)/Et$_2$NH, 100:100:20.

IR (CHCl$_3$) cm$^{-1}$ 3510, 3395, 2980, 2950, 1740, 1660, 1535, 1460, 1370, 1240, 1170, 1045.

$^1$H NMR (300 MHz, CDCl$_3$) δ: 6.53 (CONH), 4.94 (H-13), 4.84 (H-1"), 4.83 (H-2'), 4.66 (H-4"), 4.65 (H-1'), 4.57 (H-10), 4.36 (H-5"), 4.02 (H-3), 3.73 (H-5'), 3.47 (H-5), 3.33 (3"-OCH$_3$), 2.78 (H-3'), 2.53 (H-2), 2.40 (H-2"a), 2.27/3'-N(CH$_3$)$_2$/, 2.14 (H-8), 2.13, 2.12, 2.07, 2.05 and 2.02 (COCH$_3$), 1.92 (H-4), 1.83 (H-14a), 1.73 (H-4'a), 1.56 (H-2"b), 1.50 (H-7a), 1.44 (H-14b), 1.36 (H-4'b), 1.28 (6-CH$_3$), 1.26 (H-7b), 1.22 (5'-CH$_3$), 1.20 (12-CH$_3$), 1.15 (2-CH$_3$), 1.13 (10-CH$_3$), 1.11 (3"-CH$_3$), 1.11 (5"-CH$_3$), 1.02 (8-CH$_3$), 0.98 (4-CH$_3$), 0.89 (15-CH$_3$).

What is claimed is:

1. A compound represented by formula (I),

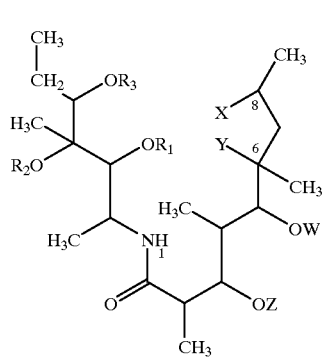

(I)

and its pharmaceuticaly acceptable addition salts with inorganic or organic acids, wherein R$_1$ represents hydrogen, C$_1$–C$_4$ alkanoyl group, arylcarbonyl group and together with R$_2$ and carbon atoms to which they are bound, cyclic carbonyl or thiocarbonyl group, R$_2$ represents hydrogen or together with R$_1$ and carbon atoms to which they are bound, cyclic carbonyl or thiocarbonyl group, R$_3$ represents hydrogen, C$_1$–C$_4$ alkanoyl or arylcarbonyl group, Z is hydrogen or L-cladinosyl group represented by formula (i)

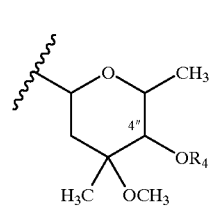

(i)

wherein R$_4$ represents hydrogen or C$_1$–C$_4$ alkanoyl group,
W is hydrogen or D-desosaminyl group represented by formula (ii)

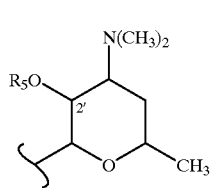

(ii)

wherein R$_5$ represents hydrogen or C$_{1-4}$C alkanoyl or arylcarbonyl group,

X and Y together represent a lactone, or X is CH$_2$OR$_6$, wherein R$_6$ represents hydrogen or C$_1$–C$_4$ alkanoyl group and Y is hydroxyl group.

2. A compound according to claim 1, characterized in that R$_1$, R$_2$ and R$_3$ are the same and represent hydrogen, Z is hydrogen or L-cladinosyl group represented by formula (i), wherein R$_4$ is hydrogen, W is hydrogen or D-desosaminyl group represented by formula (ii), wherein R$_5$ is hydrogen, and X and Y together represent a lactone.

3. A compound according to claim 1, characterized in that Z is L-cladinosyl group represented by formula (i), wherein R$_4$ is hydrogen and W is D-desosaminyl group represented by formula (ii), wherein R$_5$ is hydrogen.

4. A compound according to claim 1, characterized in that Z is hydrogen and W is D-desosaminyl group represented by formula (ii), wherein $R_5$ is hydrogen.

5. A compound according to claim 1, characterized in that Z and W are the same and represent hydrogen.

6. A compound according to claim 1, characterized in that $R_1$ and $R_3$ are the same and represent $C_1$–$C_4$ alkanoyl group, $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ represents hydrogen or $C_1$–$C_4$ alkanoyl group, and X and Y together represent lactone.

7. A compound according to claim 6, characterized in that $R_1$ and $R_3$ are the same and represent acetyl group, $R_2$ is hydrogen, Z is L-cladinosyl group represented by formula (i), wherein $R_4$ represents acetyl group, W is D-desosaminyl group represented by formula (ii), wherein $R_5$ represents hydrogen.

8. A compound according to claim 6, characterized in that $R_1$ and $R_3$ are the same and represent acetyl group, $R_2$ is hydrogen, Z is L-cladinosyl group represented by formula (i), wherein $R_4$ represents acetyl group, W is D-desosaminyl group represented by formula (ii), wherein $R_5$ represents acetyl group.

9. A compound according to claim 1, characterized in that $R_1$ and $R_3$ are the same or different and represent hydrogen, $C_1$–$C_4$ alkanoyl group or arylcarbonyl group, $R_2$ is hydrogen, Z is L-cladinosyl group represented by formula (i), wherein $R_4$ represents hydrogen or $C_1$–$C_4$ alkanoyl group, W is D-desosaminyl group represented by formula (ii), wherein $R_5$ represents hydrogen or arylcarbonyl group, and X and Y together represent lactone.

10. A compound according to claim 9, characterized in that $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ represents 4-bromobenzoyl group.

11. A compound according to claim 9, characterized in that $R_1$ and $R_3$ are the same and represent acetyl group, $R_2$ is hydrogen, Z is L-cladinosyl group represented by formula (i), wherein $R_4$ represents acetyl group, W is D-desosaminyl group represented by formula (ii), wherein $R_5$ represents 4-bromobenzoyl group.

12. A compound according to claim 9, characterized in that $R_1$ is 4-bromobenzoyl group, $R_2$ and $R_3$ are t he same and represent hydrogen, Z is L-cladinosyl group represented by formula (i), wherein $R_4$ is hydrogen, W is D-desosaminyl group represented by formula (ii), wherein $R_5$ represents 4-bromobenzoyl group.

13. A compound according to claim 9, characterized in that $R_1$ is 4-bromobenzoyl group, $R_2$ and $R_3$ are the same and represent hydrogen, Z is L-cladinosyl group represented by formula (i), wherein $R_4$ is hydrogen W is D-desosaminyl group represented by formula (ii), wherein $R_5$ is hydrogen.

14. A compound according to claim 9, characterized in that $R_3$ is 4-bromobenzoyl group, $R_1$ and $R_2$ are the same and represent hydrogen, Z is L-cladinosyl group represented by formula (i), wherein $R_4$ is hydrogen, W is D-desosaminyl group represented by formula (ii), wherein $R_5$ represents 4-bromobenzoyl group.

15. A compound according to claim 9, characterized in that $R_3$ is 4-bromobenzoyl group, $R_1$ and $R_2$ are the same and represent hydrogen, Z is L-cladinosyl group represented by formula (i), wherein $R_4$ is hydrogen, W is D-desosaminyl group represented by formula (ji), wherein $R_5$ is hydrogen.

16. A compound according to claim 1, characterized in that $R_1$ and $R_2$ together with carbon atoms to which they are bound represent cyclic carbonyl or thiocarbonyl group, $R_3$ is hydrogen, Z is L-cladinosyl group represented by formula (i), wherein $R_4$ is hydrogen, W is D-desosaminyl group represented by formula (ii), wherein $R_5$ is hydrogen, and X and Y together represent lactone.

17. A compound according to claim 16, characterized in that $R_1$ and $R_2$ together with carbon atoms to which they are bound represent cyclic carbonyl group and $R_3$ is hydrogen.

18. A compound according to claim 1, characterized in that $R_1$ and $R_3$ are the same and represent hydrogen or $C_1$–$C_4$ alkanoyl group, $R_2$ is hydrogen, Z is L-cladinosyl group represented by formula (i), wherein $R_4$ is hydrogen, or represents $C_1$–$C_4$ alkanoyl group, W is D-desosaminyl group represented by formula (ii), wherein $R_5$ is hydrogen, or represents $C_1$–$C_4$ alkanoyl group, X is $CH_2OR_6$ group, wherein $R_6$ represents hydrogen, or represents $C_1$–$C_4$ alkanoyl group and Y is hydroxyl group.

19. A compound according to claim 18, characterized in that $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ is hydrogen, X is $CH_2OR_6$ group, wherein $R_6$ is hydrogen, and Y is hydroxyl group.

20. A compound according to claim 18, characterized in that $R_1$ and $R_3$ are the same and represent acetyl group and $R_2$ is hydrogen, Z is L-cladinosyl group represented by formula (i), wherein $R_4$ represents acetyl group, W is D-desosaminyl group represented by formula (ii), wherein $R_5$ represents acetyl group, X is $CH_2OR_6$ group, wherein $R_6$ is acetyl group, and Y is hydroxyl group.

21. A process for the preparation of a compound of the formula (I),

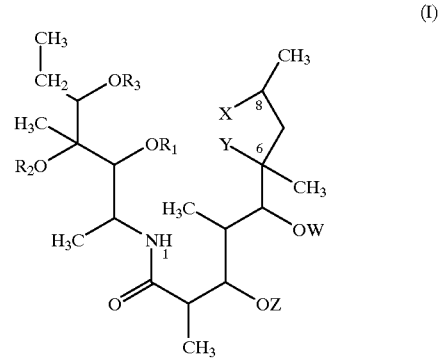

or its pharmaceutically acceptable salts with inorganic or organic acids, wherein $R_1$ represents hydrogen, $C_1$–$C_4$ alkanoyl group, arylcarbonyl group or together with $R_2$ and carbon atoms to which they are bound, cyclic carbonyl or thiocarbonyl group, $R_2$ represents hydrogen or together with $R_1$ and carbon atoms to which they are bound, cyclic carbonyl or thiocarbonyl group, $R_3$ represents hydrogen, $C_1$–$C_4$ alkanoyl or arylcarbonyl group, Z is hydrogen or L-cladinosyl group represented by formula (i)

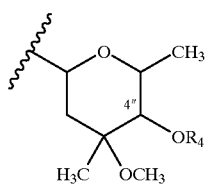

(i)

wherein $R_4$ represents hydrogen or $C_1$–$C_4$ alkanoyl group, W is hydrogen or D-desoaminyl group represented by formula (ii)

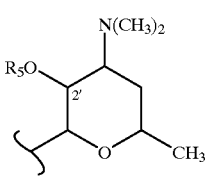

(ii)

wherein $R_5$ represents hydrogen or $C_1$–$C_4$ alkanoyl or arylcarbonyl group, X and Y together represent lactone or X is $CH_2OR_6$ group, wherein $R_6$ represents hydrogen, or $C_1$–$C_4$ alkanoyl group and Y is hydroxyl group, characterized in that 6-deoxy-6,9-epoxy-8(R)-methyl-10-amino-9,10-secoerythromycin A of formula (II)

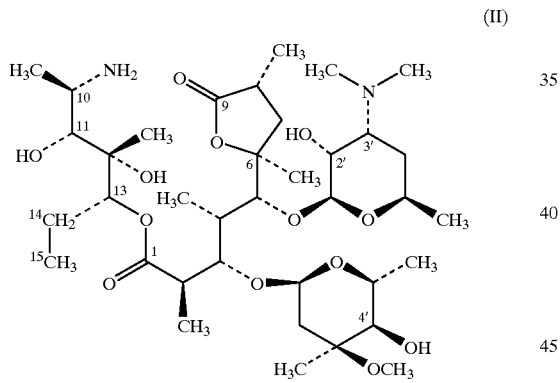

(II)

is subjected to the action of a polar solvent for a period of time required that by internal transacylation a compound of the formula (I) is formed, wherein $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ is hydrogen, and X and Y together represent lactone group, which is subsequently, if required, subjected to A/ a reaction with diluted inorganic acid at room temperature, yielding a compound of the formula (I), wherein $R_1$, $R_2$ and $R_3$ are the same and represent hydrogen, Z is hydrogen, W is D-desoaminyl group represented by formula (ii), wherein $R_5$ is hydrogen, and X and Y together represent lactone, or a reaction with a more concentrated acid in presence of an inert solvent at an increased temperature yielding a compound of the formula (I), wherein $R_1$, $R_2$ and $R_3$ are the same and represent hydrogen, Z and W are the same and represent hydrogen, and X and Y together represent lactone, or B/ subjected to O-acylation with an anhydride or chloride ot a carboxylic acid, yielding a compound of formula (I)

B1/ by being subjected to O-acylation with anhydride or chloride of $C_1$–$C_4$ alkylcarboxylic acid in a reaction-inert solvent at a temperature of 0–30° C., thereby yielding a compound ot the formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ represents $C_1$–$C_4$ alkanoyl group, and X and Y together represent a lactone which is subsequently, if required, subjected to a reaction of solvolysis in lower alcohol at room temperature for 3 days., yielding a compound of the formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ is hydrogen, and X and Y together represent lactone, or yielding B2/ by being subjected to O-acylation with a chloride of arylcarboxylic acid, a compound of formula (I) in accordance with B2a/ being subjected to at least 1.1 equimolar excess of acid chloride in dry acetone, at temperature 0–5° C., thereby yielding a compound of the formula (I), wherein $R_1$, $R_2$ and $R_3$ are the same and represent hydrogen, Z is L-cladinosyl group represented by formula (i), wherein $R_4$ is hydrogen, W is D-desosaminyl group represented by formula (ii), wherein $R_5$ represents arylcarbonyl group and X and Y together represent lactone, which is subsequently, if required, subjected to an O-acylation according to B1/ with acetic acid anhydride yielding a compound of the formula (I), wherein $R_1$ and $R_3$ are the same and represent $C_1$–$C_4$ alkanoyl group and $R_2$ is hydrogen, Z is L-cladinosyl group represented by formula (i), wherein $R_4$ represents $C_1$–$C_4$ alkanoyl group, W is D-desosaminyl group represented by formula (ii), wherein $R_5$ represents arylcarbonyl group, and X and Y together represent lactone, or in accordance with B2b/ being subjected to at least 5 equimolar excess of an acid chloride at an increased temperature, thereby yielding a mixture of compounds of the formula (I), wherein $R_1$ represents arylcarbonyl group, and $R_1$ and $R_3$ are the same and represent hydrogen, or wherein $R_3$ represents arylcarbonyl group, and $R_1$ and $R_2$ are the same and represent hydrogen, Z is L-cladinosyl group represented by formula (i), wherein $R_4$ is hydrogen and W is D-desosaminyl group represented by formula (ii), wherein $R_5$ represents arylcarbonyl group, and X and Y together represent lactone, which are compounds separated by chromatography on a silica gel column and subsequently, if required, subjected to a reaction of solvolysis, yielding a compound of the formula (I), wherein $R_1$ represents arylcarbonyl group, and $R_2$ and $R_3$ are the same and represent hydrogen, or wherein $R_3$ represents arylcarbonyl group, and $R_1$ and $R_2$ are the same and represent hydrogen, Z is L-cladinosyl group represented by formula (i), wherein $R_1$ is hydrogen and W is D-desosaminyl group represented by formula (ii), wherein $R_5$ is hydrogen, and X and Y together represent lactone, or C/ a reaction of transesterification with a carboxylic acid derivative in an inert solvent at an increased temperature for 3–9 hours, yielding a compound of the formula (I), wherein $R_1$ and $R_2$ together with carbon atoms, to which they are bound, represent cyclic carbonyl or thiocarbonyl group and $R_3$ is hydrogen, Z is L-cladinosyl group represented by formula (i), wherein $R_4$ is hydrogen, W is D-desoaminyl group represented by formula (ii), wherein R, is hydrogen and X and Y together represent lactone, or D/ a reduction with a complex metal hydride in the presence of a tertiary alcohol in an inert solvent at an increased temperature a compound of the formula (I), wherein $R_1$, $R_2$ and $R_3$ are the same and represent hydrogen, Z is L-cladinosyl group represented by formula (i), wherein $R_4$ is hydrogen, W is D-desoaminyl group represented by formula (ii), wherein $R_5$ is hydrogen and X is $CH_2OR$, group, wherein R, is hydrogen, and Y is hydroxyl group, which is subsequently, if required, subjected to O-acylation according to B1/ yielding a compound ot the general formula (I), wherein $R_1$ and $R_3$ are the same and represent $C_1$–$C_4$ alkanoyl group, $R_2$ is hydrogen and Z is L-cladinosyl group represented by formula (i), wherein $R_4$ presents $C_1$–$C_4$ alkanoyl group, W is D-desoaminyl group represented by formula (ii), wherein $R_5$ represents $C_1$–$C_4$ alkanoyl group, X is $CH_2OR_6$ group, wherein $R_6$ is $C_1$–$C_4$ alkanoyl group and Y is hydroxyl group, and subsequently, if required, the obtained secomacrolides are subjected to a reaction with an at least equimolar amount of the corresponding inorganic or organic acid, in a reaction-inert solvent, yielding the corresponding addition salts.

22. The process of claim 21 wherein the diluted inorganic acid is 0.25 N hydrochloric acid.

23. The process of claim 21 wherein the more concentrated acid is 2 N hydrochloric acid.

24. The process of claim 21 wherein the inert solvent in step A comprises chloroform and the increased temperature is reflux temperature of the reaction mixture.

25. The process of claim 21 wherein the lower alcohol in step B1 comprises methanol.

26. The process of claim 21 wherein the $C_1$–$C_4$ alkylcarboxylic acid comprises acetic acid anhydride in step B1.

27. The process of claim 21 wherein the reaction-insert solvent in step B1 comprises pyridine.

28. The process of claim 21 wherein the temperature in step B1 is room temperature.

29. The process of claim 21 wherein the acid chloride is 4-bromo-benzoylchloride.

30. The process of claim 21 wherein the acid chloride in step B2b is 4-bromo-benzoylchloride and the reaction is carried out at a reflux temperature of the reaction mixture.

31. The process of claim 21 wherein the carboxylic acid derivative is 3–5 equimolar excess of ethylene carbonate.

32. The process of claim 21 wherein the inert solvent in step C comprises benzene and the increased temperature is reflux temperature of the reaction mixture.

33. The process of claim 21 wherein the metal hydride in step D comprises sodium borohydride.

34. The process of claim 21 wherein the tertiary alcohol is t-butanol and the inert solvent in step D comprises methanol and the temperature is a reflux temperature of the reaction mixture.

35. The process of claim 21 wherein the O-acylation in step D is with acetic acid anhydride.

* * * * *